US00PP34811P2

(12) United States Plant Patent
Grauke et al.

(10) Patent No.: US PP34,811 P2
(45) Date of Patent: Dec. 13, 2022

(54) PECAN TREE NAMED 'PUEBLO'

(50) Latin Name: *Carya illinoinensis*
Varietal Denomination: Pueblo

(71) Applicant: The United States of America, as represented by the Secretary of Agriculture, Washington, DC (US)

(72) Inventors: Larry J. Grauke, College Station, TX (US); Tommy E. Thompson, College Station, TX (US); George D. Madden, Brownwood, TX (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/506,091

(22) Filed: Oct. 20, 2021

(51) Int. Cl.
*A01H 6/00* (2018.01)
*A01H 5/08* (2018.01)

(52) U.S. Cl.
USPC ..... Plt./153

(58) Field of Classification Search
USPC ..... Plt./153
CPC ..... A01H 6/00; A01H 5/08
See application file for complete search history.

*Primary Examiner* — Keith O. Robinson
(74) *Attorney, Agent, or Firm* — John Fado; Maria Restrepo-Hartwig

(57) ABSTRACT

A new and distinct variety of pecan tree, denominated 'Pueblo', having a columnar tree shape with a nut crop centered in the core of the tree, high precocity, medium-sized nut clusters, early pollen shed, early bud break, and high resistance to scab fungus (*Venturia effusa*).

8 Drawing Sheets

Latin name of the genus and species of the plant claimed: 'Pueblo' is a pecan tree that is a *Carya illinoinensis.*

Variety denomination: The new pecan tree is of the variety denominated 'Pueblo'.

BACKGROUND OF THE NEW PLANT

'Pueblo', tested as 1975-08-0005, is a progeny of a 1975 cross between 'Osage' (not patented) and 'Creek' (not patented) pecan cultivars. The seedling was initially grown in Brownwood, Tex. and was selected for further testing due to precocity and early nut maturity. 'Pueblo' has been evaluated most extensively in orchards in Burleson County, Tex., in a replicated test that had six blocks, with 35 entries occurring once per block. 'Pueblo' has also been studied in orchards in Hempstead, Tex., and it has also been tested by cooperators in Kansas and Indiana. The establishment of orchards with increased tree density made possible by a columnar tree shape will accentuate the high precocity of this selection, increasing profit in the early life of orchards. Concentrating crop in the central core of a columnar tree and distributing it among many medium-sized clusters may be an appropriate architecture for western orchards that are hedged and receive high light intensity.

SUMMARY OF THE INVENTION

'Pueblo' is distinguished from other pecan varieties due to the following unique combination of characteristics: a columnar tree shape with a nut crop centered in the core of the tree, high precocity, medium-sized nut clusters, early pollen shed, early bud break, and high resistance to scab fungus (*Venturia effusa*). 'Pueblo' has not been observed under all environmental conditions and cultural practices, and some characteristics may differ outside of Central Texas or with different management practices.

BRIEF DESCRIPTION OF THE FIGURES

The accompanying drawings include color photographs that are as nearly true as it is reasonably possible to make in a color illustration of this type.

FIG. **4*a*** is photograph of a red pistillate flower and a mottled red/green 'Pueblo' pistillate flower. Photo taken in Burleson County, Tex. on Apr. 19, 2021.

FIG. **4*b*** is a photograph of a mottled red/green 'Pueblo' pistillate flower. Photo taken in Burleson County, Tex. on Apr. 19, 2021.

Figure 5:
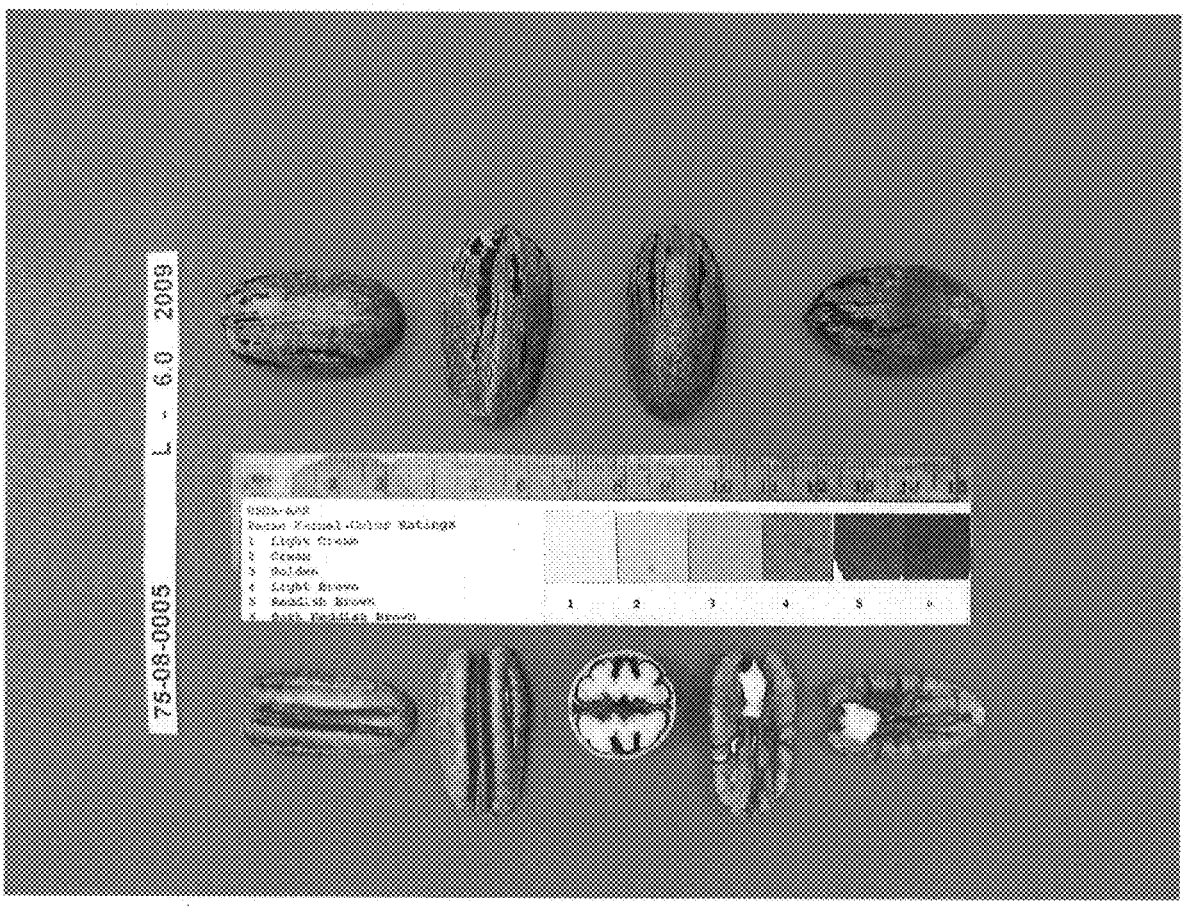

FIG. 5 is a photograph of a nut panel of 'Pueblo'. Photo taken in Brownwood, Tex. on Apr. 25, 2010. The nut sample was collected in 2009 from tree L-6, Fangue Orchard, Hempstead, Waller County.

Figure 6:
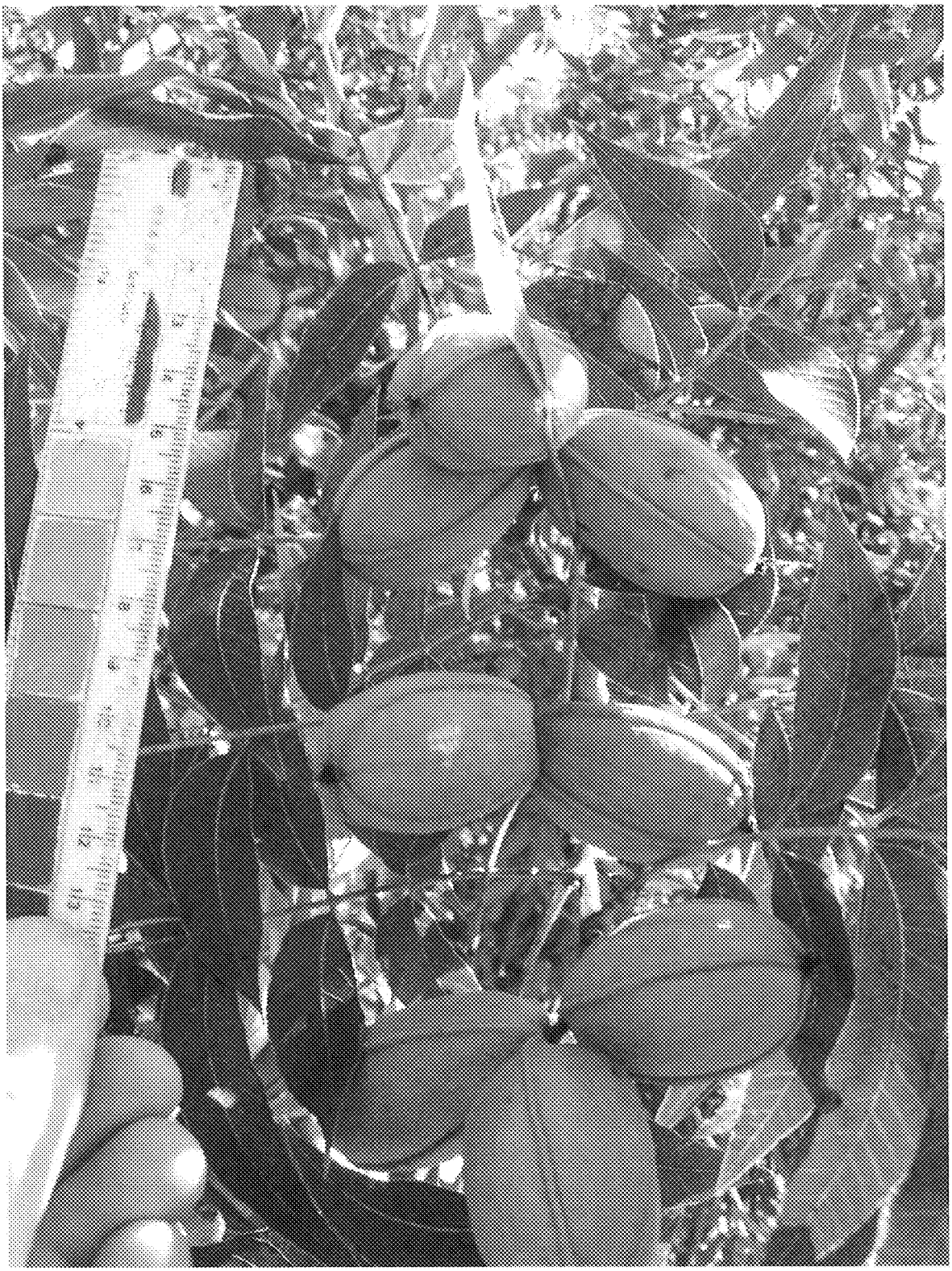

FIG. 6 is a photograph of the nut clusters of 'Pueblo' (Fangue Orchard, tree D-13. Photo taken in Waller County, Tex. on Sep. 9, 2011.

Figure 7:
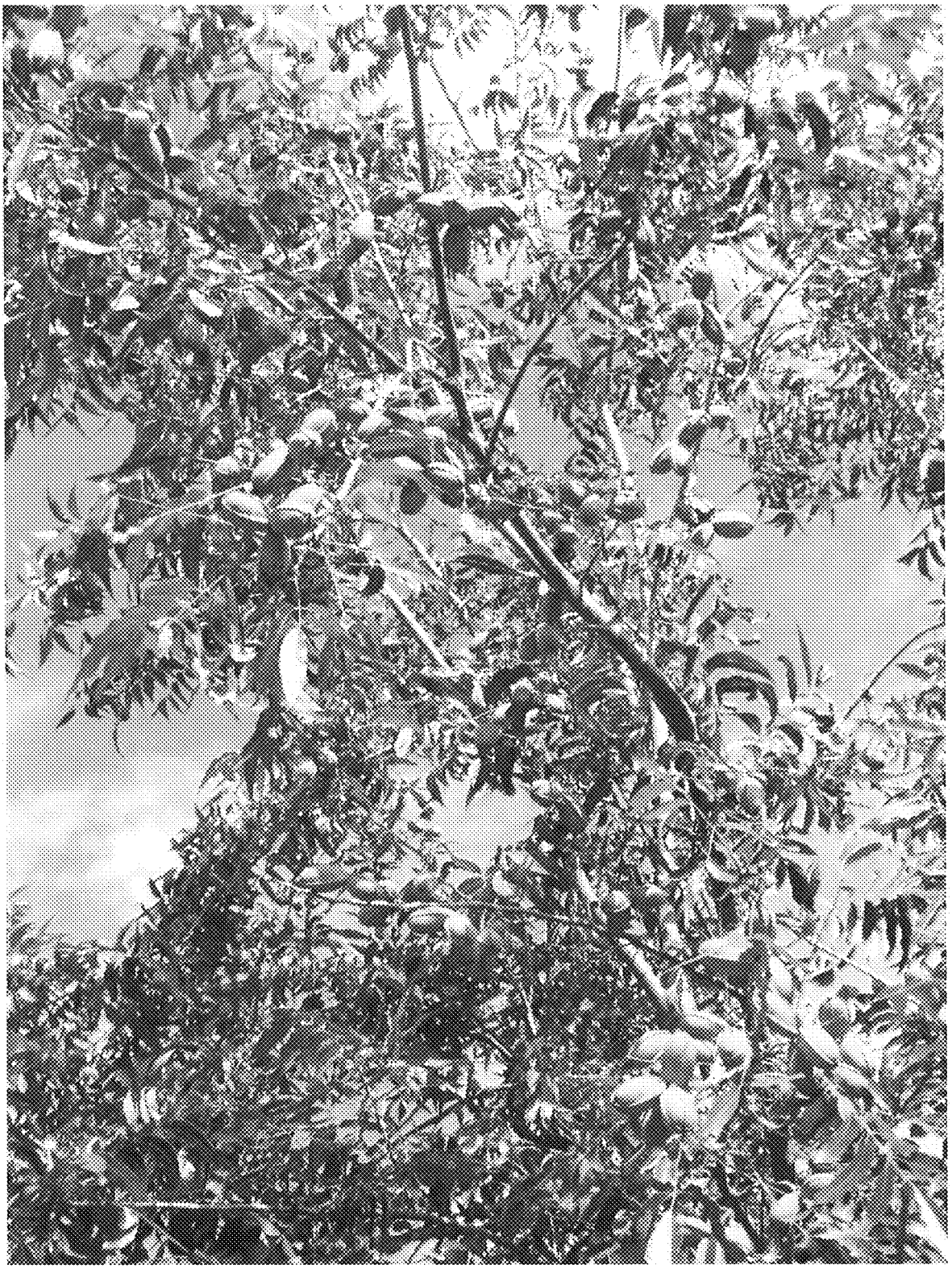

FIG. 7 is a photograph of a nut crop concentrated in the core of a 'Pueblo' tree canopy (Fangue Orchard, tree F-17. Photo taken in Waller County, Tex. on Sep. 8, 2008. Age of scion was 6 years.

Figure 8:
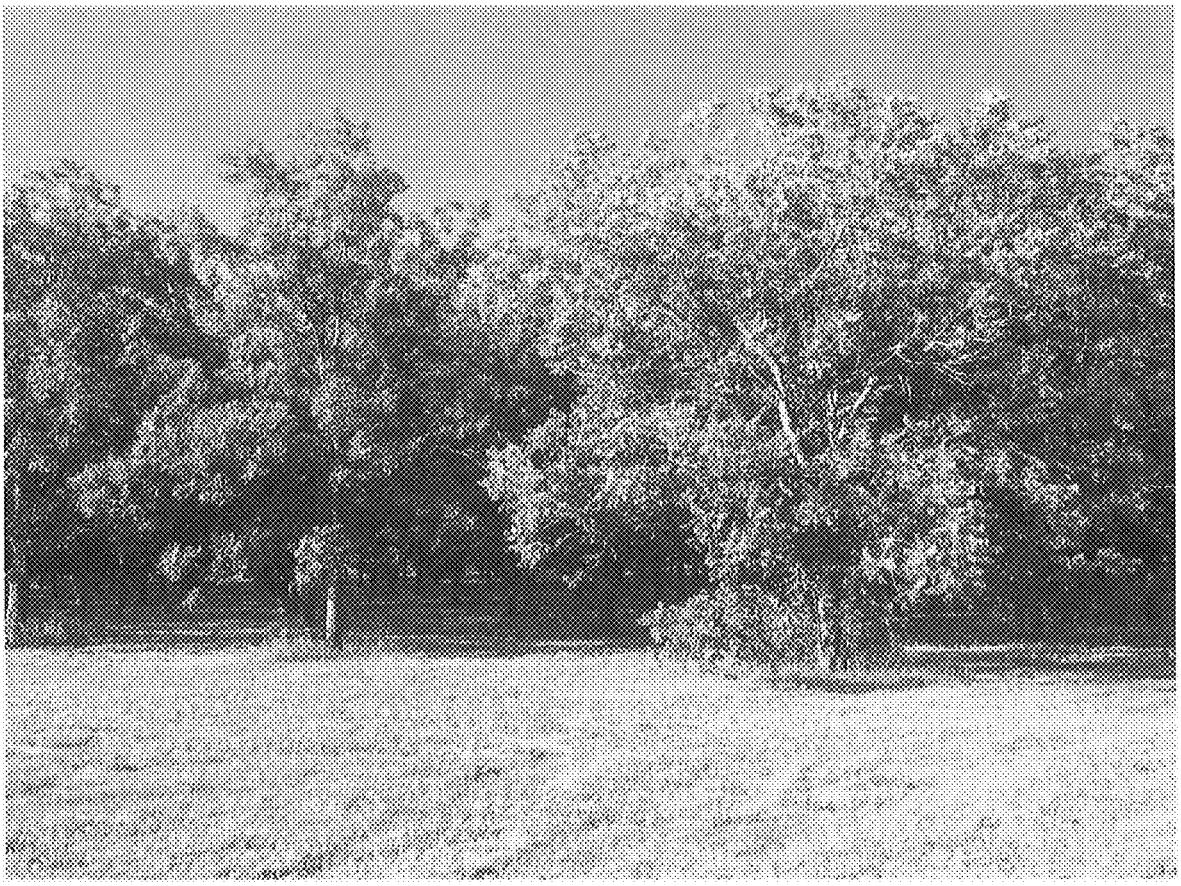

FIG. 8 is a photograph of a 'Pueblo' tree (left) next to a 'Choctaw' (not patented) tree (right). Photo taken in Burleson County, Tex. on Aug. 22, 2019. Age of the scions at that time was 27 years (on roots that were 34 years old).

Due to photographical light, chemical development, processing and printing, the leaves and fruit depicted in these photographs may or may not be accurate when compared to the actual botanical specimen.

DETAILED BOTANICAL DESCRIPTION

All color descriptions are based off of the Munsell Plant Tissue Color Book: 2012 Year Revision (2019 Printing).

The botanical description below is based on 6 grafted clones of 'Pueblo' located in the same orchard in Burleson County, Tex. There is no living ortet for 'Pueblo'. Unless otherwise noted, the observations below were collected in 2021 (29 years after grafting).

Parentage:

*Seed parent*.—'Osage'.

*Pollen parent*.—'Creek'.

Tree a. *Overall shape*.—General shape and height to width ratio: average 1.98. Tree shape is columnar, with narrow canopy shape permitting increased tree density without crowding.

b. *Vigor*.—Vigorous. 'Pueblo' was fruiting 2 years after grafting.

c. *Height*.—Trees were hedged in 2009, last pre-hedging height measurement was in 2002. Average Height: 9.93 m (2002, 10 yrs). Average Height: 18.25 m (2021, 29 yrs).

d. *Width/trunk diameter*.—i. Canopy Width: 7.2 m. ii. Trunk Diameter: 306 mm.

e. *Trunk bark texture*.—Scaly when Mature.

f. *Trunk bark color*.—2.5Y 5/2.

g. *Branch color*.—i. Woody stage branch shoots: 2.5Y 5/2. ii. Lenticels: Lenticel shape is highly variable. An average length would be 1.2 mm. The average width would be 0.9 mm. iii. Lenticel Color: 7.5YR 5/4.

h. *Internodes*.—The average length between the $3^{rd}$ and $4^{th}$ leaf from the base of the shoot is 7.66 mm.

i. *Disease and insect resistance*.—i. Pecan Scab, *Venturia effusa* (leaf and nut), data from 1994-2007. In our unsprayed orchards, 'Pueblo' has had only trace amounts of either leaf or nut scab. ii. Blackmargined Aphid, *Monetlia caryella* (leaf), data from 2008-2009. 'Pueblo' was comparable to 'Pawnee' (not patented) in resistance to blackmargined aphids (Skrivanek et al. 2013).

j. *Leaves* (*data from June* 2021).—i. Leaf Arrangement and Color. 1. Leaves are odd-pinnately compound opposite. 2. Upper leaf color is 7.5GY 3/4. 3. Lower leaf color is 5GY 4/4. ii. The number of leaves per shoot and the number of leaflets per mature leaf. 1. Leaves per shoot: 9-16, Average 12. 2. Leaflets per leaf: 9-13, Average 11. iii. The angle of leaflet pairs to the rachis: 45°. iv. Leaflet blade: flat and not convoluted. v. Length and width of a mature leaf ($4^{th}$ leaf from the base of the shoot). 1. Length Range: 189-374 mm. Average: 269 mm. 2. Width Range: 170-243 mm. Average: 223 mm. vi. Petiole shape and color. Petiole shape is circular. Petiole color is 2.5GY 6/8. vii. Petiole length of the $4^{th}$ leaf from the base. 1. Length Range: 34-50 mm. Average: 41 mm. 2. Width Range: 1.4-1.9 mm. Average: 1.66 mm viii. Leaflet size and shape ($4^{th}$ leaflet on $4^{th}$ leaf). 1. Leaflet Size Range: 81-137 mm. Average: 107 mm. 2. Width Size Range: 23-37 mm. Average: 26 mm. 3. Leaflet shape is falcate with serrate margins, an oblique base, and acuminate tip. ix. Texture of upper leaf. The leaf texture is smooth on both the upper and lower surfaces with a glossy sheen. x. Sheen: glossy. xi. Petiolule. 1. Petiolule Length Range: 1.33-3.68 mm. Average: 2.17 mm. 2. Petiolule Width Range: 0.82-1.3 mm. Average: 1.02 mm. xii. Margin: Leaf margin is serrate. xiii. Tip Shape: Leaf tip is acuminate. xiv. Pubescence (Upper leaf and Lower leaf). Leaf pubescence is mostly glabrous with occasional pilose regions.

Inflorescence:

a. *General description*.—'Pueblo' is monoecious, anemophilous, and protandrous (Table 1).

b. *Flowers*.—i. The number of pistillate flowers and arrangement of the flowers. 1-4 individual pistillate flowers per pedicel spike are borne alternately on terminally positioned spikes. ii. Description of the pistillate flower and pedicels. Late pistil receptivity with reflexed, red stigmas. iii. Staminate catkin length and width (in mm). 1. Catkin Length Range: 25-65 mm. Average: 46.1 mm. 2. Catkin Width Range: 3-4 mm. Average: 3.1 mm. iv. Staminate color, pollen color. 1. Staminate color: 2.5GY 6/10. 2. Pollen color: 5Y 8/10. v. Involucre size, including the stigma (length and width). 1. Involucre Length Range: 9.76-10.48 mm. Involucre Length Average: 10.12 mm. 2. Involucre Width Range: 2.62-3.04 mm. Involucre Width Average: 2.83 mm. vi. Description of Anthocyan on stigma. The stigmas are red sometimes containing patches of green. vii. Flower pistil color(s). Dominant stigma color is red (5R 4/6) with occasional splashes of green (5GY 5/6). viii. Number and color of bracts, shape (lanceolate), flower length and width, and description of petal fusion and the end resulting flower shape (copular involucre): Three lanceolate bracteoles are present and one bract (all color: 5G 4/8), the bract is at least twice as long the three bracteoles. The bracteoles and bract are fused at the base to form a copular involucre.

Fruit:

a. *Mature fruit*.—Is dehiscent.

b. *Shuck*.—i. Shuck color is 7.5GY 6/8. ii. Shucks open widely during dehiscence.

c. *Fruit split*.—During water stage has not been observed to be a problem.

d. *Shuck decline*.—During kernel formation has not been observed to be a problem.

Nuts:

a. *Observations are from detailed measurements of five nuts per year from multiple years*.—1994-1999, 2001, 2003, and 2005.

b. *Size*.—i. The average nut length is about 43 mm. The average nut width is about 23 mm. The length-to-width ratio is 1.91. ii. Nut cross-section is round with a flatness ratio (width across sutures to the width between sutures) of 1.02.

c. *Form*.—i. The shape of the nut with the shape of the cross-section. The nut is oblong-elliptic shaped (length to height ratio 1.96) with a round cross section. ii. Base shape: Oblique. iii. Apex shape: Oblique. iv. Presence and locations of defining features: Nut apex is slightly grooved. v. Description of shell suture: Often, but not always, elevated. vi. Description of shell surface: Black (5R 0/0) lines and patches stretch from the apex to the midpoint of the nut, covering up to 50% of the upper nut surface. vii. Description of shell topography: Smooth.

d. *Dorsal grooves*.—Kernels have deep, but wide dorsal grooves that do not trap packing material.
e. *Ventral grooves*.—Kernels have a narrow, shallow ventral groove.
f. *Weight*.—8.49 g.
g. *Cluster size*.—On average 1.87 nuts per cluster
h. *Shell topography*.—Generally smooth, with a slight ridge on the suture.
i. *Shell thickness*.—0.98 mm average, moderately thick.
j. *Shell color*.—7.5YR 4/4.
k. *Kernel color*.—Golden kernel color: 7.5YR 6/4.
l. *Kernel percentage*.—54.8% Average.
m. *Nut maturity date*.—September 19th.
n. *Harvest ability*.—Nuts from 'Pueblo' mature in a uniform timeline.

COMPARISON TO OTHER VARIETIES

Figure 1:
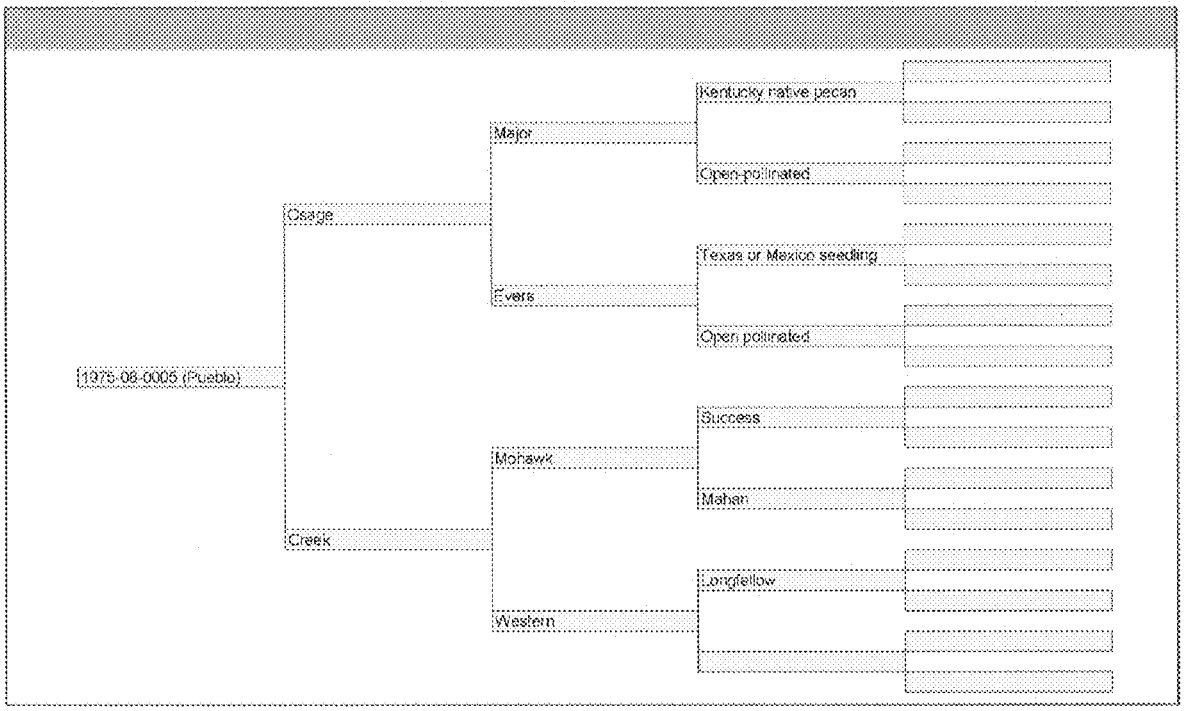
FIG. 1 is a chart showing the pedigree of 'Pueblo'. The upper branch depicts the known ancestry of the seed parent ('Osage'). The lower branch depicts the known ancestry of the pollen parent ('Creek').
Figure 2:
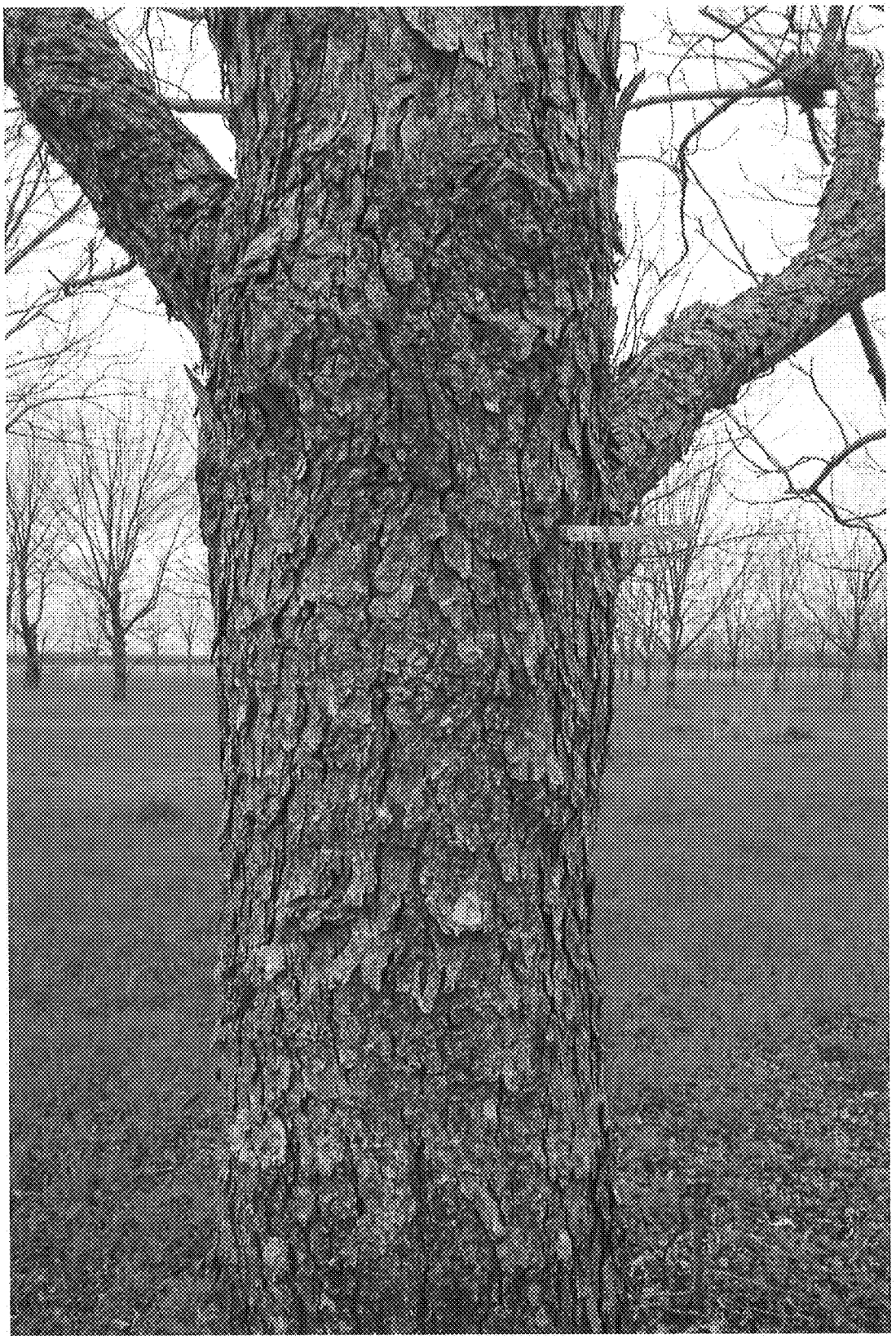
FIG. 2 is a photograph showing scaly bark of 'Pueblo'. Photo taken in Burleson County, Tex. on Mar. 22, 2021. Age of rootstock at that time was 36 years. Age of the scion was 29 years.
Figure 3:
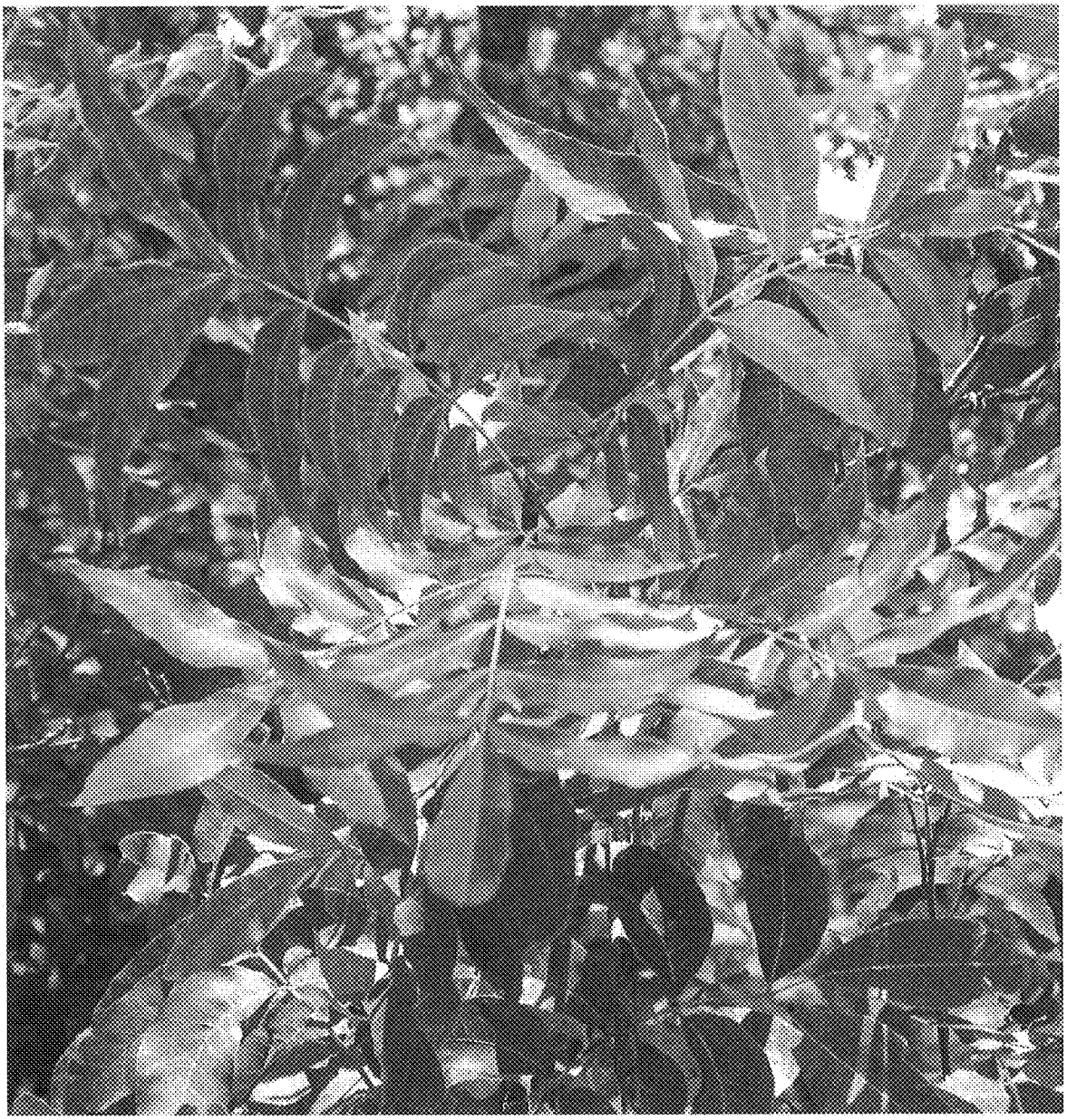
FIG. 3 is a photograph of leaf architecture of 'Pueblo'. Photo taken in Burleson County, Tex. on Aug. 10, 2021.

'Pueblo' is a new pecan cultivar that is characterized by its precocious, regular, and prolific production of good quality nuts allowing early harvest from a compact tree with a columnar canopy. Its narrow canopy shape permits planting trees at an increased density without crowding. The time of spring bud break for 'Pueblo' is generally late March in Burleson County, Tex., before the bud break of any other standard cultivars in our test (Table 2) and is about 11 days ahead of 'Pawnee'. No damage has been observed from late spring freezes—including a prolonged freeze in Texas in early February 2021. 'Pueblo' has been tested as far north as southeastern Kansas and performs well. 'Pueblo' has dark forest green leaves comparable to 'Pawnee'. Leaflet orientation is similar to most pecan trees, wherein the opposite leaflet pairs are oriented about 45 degrees from the rachis (FIG. 3).

Figure 4A:
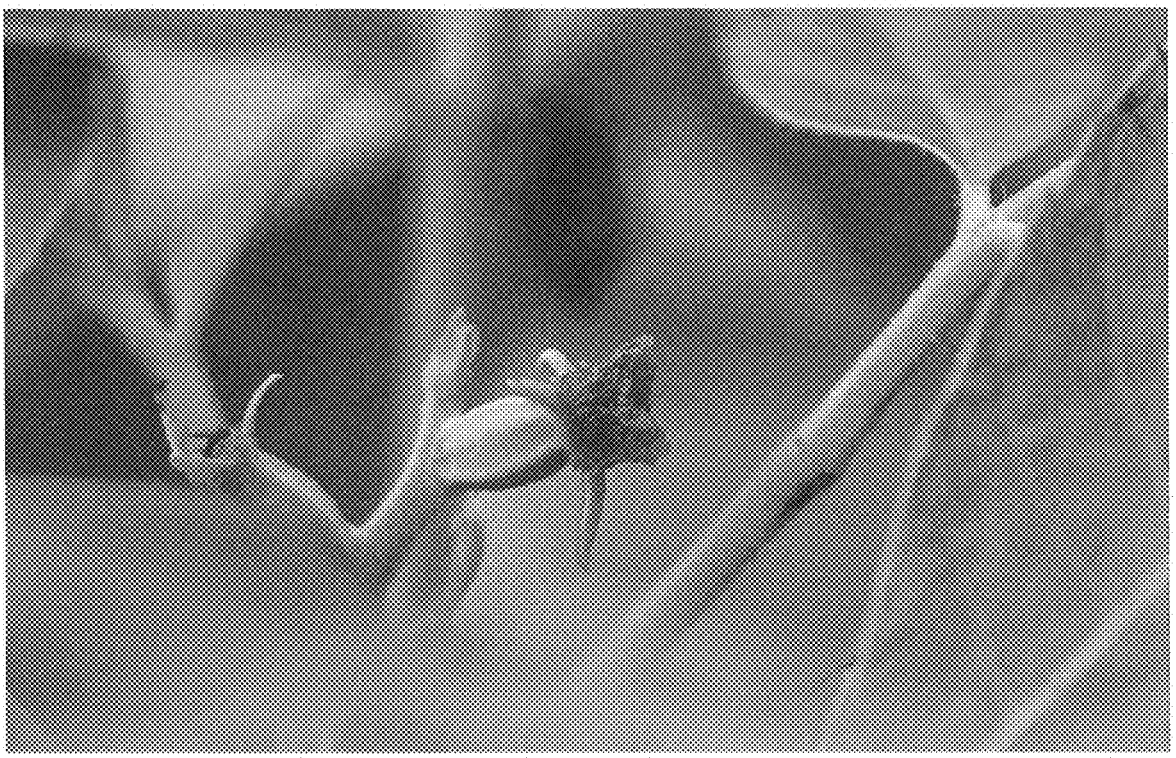
Figure 4B:
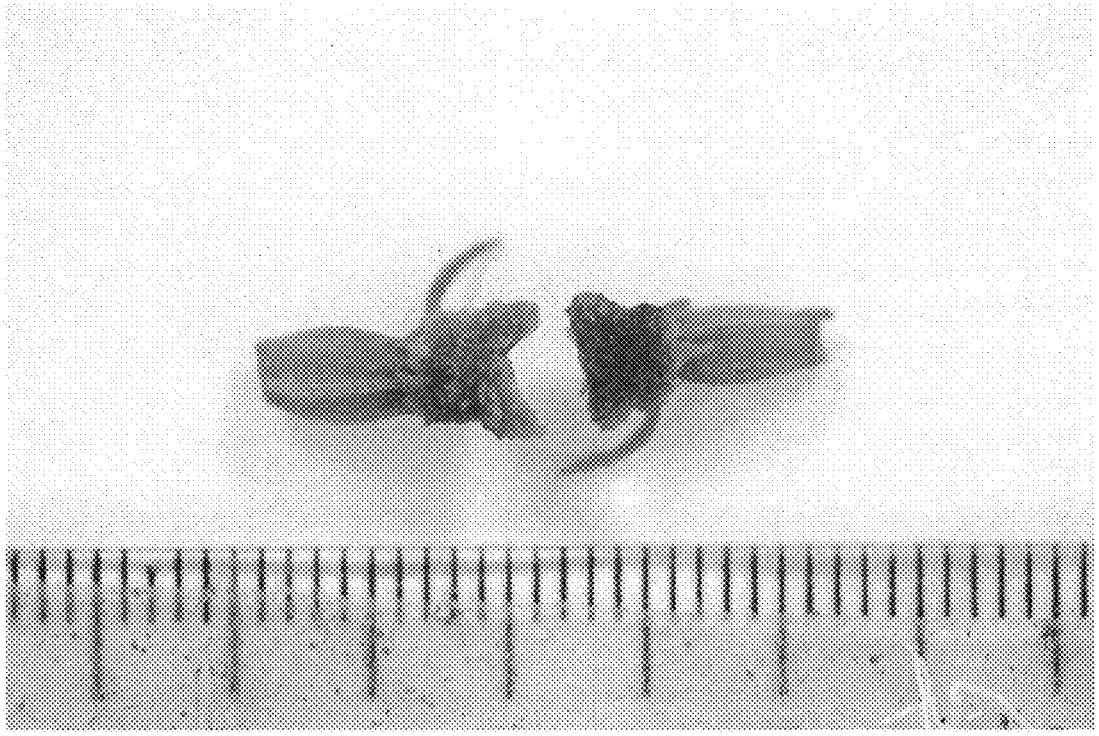

'Pueblo' is protandrous, with early pollen shed and late pistil receptivity (Table 1), slightly ahead of 'Pawnee'. It usually bears 1-4 alternately-positioned pistillate flowers per pedicel spike. 'Pueblo' has pistillate flowers with reflexed, red stigmas, similar to its pollen parent 'Creek', but contrasting to the green stigmas of its female parent 'Osage'. Some flowers exhibited a more mottled coloration of patches of green and red (FIG. 4).

Within the fungicide-treated orchards in Burleson County, Tex., 'Pueblo' exhibited similar leaf scab fungus susceptibility to the other cultivars in the test and displayed resistance to nut scab comparable to 'Houma' (not patented) but greater than 'Pawnee' (Table 3). In addition, its seed parent, 'Osage' and pollen parent 'Creek', both have excellent scab resistance. However, 'Pueblo' is likely to require fungicide management in more humid environments.

'Pueblo' has been a consistent producer of good quality nuts that mature early and are ready to harvest in mid-September in Central Texas, at the same time as 'Pawnee' (Table 4). The seed parent 'Osage' bears many small nuts very early (about a week before 'Pawnee'), while the pollen parent 'Creek' bears in early to mid-September. The average nut weight is 8.5 grams for 'Pueblo', compared to 10.3 g for 'Desirable' and 9.4 for 'Pawnee'. The average number of nuts per pound is 53.8 for 'Pueblo' compared to 44.4 for 'Desirable' (not patented) and 48.9 for 'Pawnee'. 'Pueblo' has a slightly longer nut than 'Desirable' and 'Choctaw' (not patented) and is slightly shorter than 'Pawnee' with a similar nut width to height ratio. Nut percent kernel averages 55 percent with a golden kernel color (FIG. 5). Its seed parent, 'Osage', has 54 percent kernel. 'Pueblo' also bears its nut crop throughout the tree's canopy (FIG. 7), as opposed to most pecan varieties which only bear at the growing tips. Combined with its compact shape, this tendency allows for greater yields under a hedged orchard management strategy like those commonly employed in the western United States. 'Pueblo' has medium suture wings from the base of the nut to the apex, similar to 'Stuart' (as in FIG. 6), but often with more prominent wings at the base of the nut (as is visible in FIG. 7).

Yield data indicate that 'Pueblo' has greater precocity than standard cultivars used as controls 'Choctaw', 'Desirable', 'Houma', 'Oconee' (not patented), and 'Pawnee'. Both the seed parent 'Osage' and pollen parent 'Creek' are very precocious. Yields were comparable or exceeded those of controls averaging 25.5 lbs/tree in the 6-8th leaf of the test compared to 9.3 for 'Desirable' and 10 for 'Pawnee' (Table 5). 'Pueblo' averages 2.04 nuts per cluster (with a trend of increasing nuts per cluster with age), which is less than 'Pawnee' at 2.83 nuts per cluster (Table 6). 'Pueblo' may be susceptible to overbearing with advanced age and require manual crop thinning.

Further detailed information is presented in the tables below:

TABLE 1

Period of pollen shedding and stigma receptivity of 6 pecan cultivars in 2021 in Burleson County, TX. Chart with Receptivity Windows (Y = Pollen Shed, X = Pistillate Receptivity). Type I = Protandrous. Type II = Protogynous.

| | 2nd Week April | 3rd Week April | 4th Week April | 5th Week April | 1st Week May |
|---|---|---|---|---|---|
| Choctaw | | | Y | Y | |
| (Type II) | | | X | X | |
| Desirable | | Y | Y | | |
| (Type I) | | | X | X | |
| Houma | | Y | Y | | |
| (Type I) | | | X | X | X |
| Oconee | | Y | Y | | |
| (Type I) | | | X | X | X |
| Pawnee | | Y | Y | | |
| (Type I) | | | X | X | X |
| Pueblo | Y | Y | | | |
| (Type I) | | | X | X | |

TABLE 2

Comparison of 5 yr mean date of bud break for 6 cultivars in Burleson County, TX. Data from 1997, 2000, 2001, 2005, and 2021.

| | 5 Yr Date of Bud Break Average (1997, 2000, 2001, 2005, 2021) |
|---|---|
| Choctaw | April 5th |
| Desirable | March 28th |
| Houma | March 30th |
| Oconee | March 30th |
| Pawnee | April 4th |
| Pueblo | March 24th |

TABLE 3

Comparison of average leaf and fruit scab susceptibility of 6 replicates of 6 cultivars across 7 and 11 years, respectively (data from 1994-2007) in fungicide managed orchards in Burleson County, TX. Hunter Robert's Scale: 1 = No scab lesions, 5 = Greater than 50% coverage of leaves or fruit with scab lesions.

| | 7 Yr Nut Scab Average (fungicide treated) Hunter-Roberts Scale | 11 Yr Leaf Scab Average (fungicide treated) Hunter-Roberts Scale |
|---|---|---|
| Choctaw | 2.25 | 1.83 |
| Desirable | 2.47 | 1.97 |
| Houma | 1.68 | 1.74 |
| Oconee | 2.12 | 1.93 |
| Pawnee | 3.14 | 2.03 |
| Pueblo | 1.80 | 1.95 |

TABLE 4

Comparison of average nut characteristics (Wt./nut [g], Nuts/lbs [no.], Nut length [mm], Nut Length/width, Nut flatness [ratio of nut width across suture to between suture], Kernel [percentage], Nut Maturity Date [75% shuck dehiscence] of 6 cultivars for trees in Burleson County, TX from 1994-2003.

| | Nut Length mm | Nut Weight gm | Kernel Percent | Nuts Per Lb | Shuck Split (75%) | Nut Width to Nut Height Ratio |
|---|---|---|---|---|---|---|
| Choctaw | 41.8 | 9.6 | 54.8 | 49.1 | 19-Oct. | 1.0 |
| Desirable | 41.2 | 10.3 | 53.7 | 44.4 | 18-Oct. | 1.0 |
| Houma | 38.6 | 7.8 | 47.8 | 59.0 | 26-Oct. | 1.0 |
| Oconee | 44.9 | 10.7 | 58.1 | 42.8 | 7-Oct. | 1.1 |
| Pawnee | 44.3 | 9.4 | 59.1 | 48.9 | 15-Sep. | 0.9 |
| Pueblo | 42.9 | 8.5 | 54.8 | 53.8 | 19-Sep. | 1.0 |

TABLE 5

Comparison of Average Dry Weight Nut Yield (lbs/tree) of 6 replicates of 6 cultivars growing in one orchard in Burleson County, TX from 1994-2003. Precocity (years to initial fruiting after nursery transplant) can also be interpreted from this data. These trees were grafted in 1992.

| | Yr 3 1994 | Yr 4 1995 | Yr 5 1996 | Yr 6 1997 | Yr 7 1998 |
|---|---|---|---|---|---|
| Choctaw | 0.00 | 0.97 | 1.27 | 5.63 | 0.00 |
| Desirable | 0.00 | 1.90 | 1.64 | 4.35 | 8.40 |
| Houma | 0.09 | 2.78 | 3.05 | 9.78 | 4.17 |
| Oconee | 0.00 | 0.75 | 0.56 | 0.90 | 12.73 |
| Pawnee | 0.05 | 1.57 | 3.37 | 5.75 | 18.17 |
| Pueblo | 0.34 | 5.18 | 2.31 | 15.62 | 29.67 |

| | Yr 8 1999 | Yr 9 2000 | Yr 10 2001 | Yr 12 2003 |
|---|---|---|---|---|
| Choctaw | 19.50 | 12.57 | 53.05 | 56.80 |
| Desirable | 15.13 | 17.38 | 25.58 | 55.19 |
| Houma | 23.57 | 23.90 | 9.90 | 48.60 |
| Oconee | 9.90 | 12.09 | 45.28 | 46.92 |
| Pawnee | 6.20 | 29.17 | 43.51 | 50.77 |
| Pueblo | 31.30 | 20.76 | 53.49 | 53.76 |

TABLE 6

Comparison of Average Fruit Cluster Size (Fruits/Cluster [no.]) of 6 replicates of 6 cultivars at Burleson County, TX in a four-to-five-year period (1994-2002, 2008, 2011). The 2008 and 2011 data for 'Pueblo' was reconstructed from photographs. There were no comparable photographs for the control varieties.

| | Yr 3 1994 | Yr 6 1997 | Yr 8 1999 | Yr 9 2000 | Yr 11 2002 | Yr 17 2008 | Yr 20 2011 | 7 Year Average |
|---|---|---|---|---|---|---|---|---|
| Choctaw | — | 2.80 | 2.87 | 2.37 | 1.7 | — | — | 2.43 |
| Desirable | — | 2.32 | 2.75 | 1.8 | 1.27 | — | — | 2.03 |
| Houma | 2.20 | 2.72 | 3.35 | 2.15 | 2 | — | — | 2.48 |
| Oconee | — | 1.50 | 2.07 | 1.25 | 1.3 | — | — | 1.53 |
| Pawnee | 3.00 | 3.43 | 3.17 | 2.58 | 1.98 | — | — | 2.83 |
| Pueblo | 1.80 | 2.20 | 1.97 | 1.73 | 1.65 | 2.41 | 2.53 | 2.04 |

We claim:

1. A new and distinct variety of pecan tree named 'Pueblo' as illustrated and described herein.

* * * * *